United States Patent
Blomstrom et al.

(10) Patent No.: US 11,806,986 B2
(45) Date of Patent: Nov. 7, 2023

(54) FLEXOGRAPHIC PRINTING DEVICE AND A METHOD OF SIMULTANEOUSLY PRINTING AT LEAST TWO MATERIAL WEBS HAVING DIFFERENT THICKNESSES

(71) Applicant: Essity Hygiene and Health Aktiebolag, Gothenburg (SE)

(72) Inventors: Philip Blomstrom, Gothenburg (SE); Lisa Palmqvist, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 68 days.

(21) Appl. No.: 16/982,674

(22) PCT Filed: Apr. 5, 2018

(86) PCT No.: PCT/SE2018/050357
§ 371 (c)(1),
(2) Date: Sep. 21, 2020

(87) PCT Pub. No.: WO2019/194710
PCT Pub. Date: Oct. 10, 2019

(65) Prior Publication Data
US 2021/0001619 A1 Jan. 7, 2021

(51) Int. Cl.
*B41F 5/24* (2006.01)
*B41F 13/10* (2006.01)
(Continued)

(52) U.S. Cl.
CPC ............... *B41F 5/24* (2013.01); *A61F 13/84* (2013.01); *B41F 13/10* (2013.01); *B41F 13/18* (2013.01);
(Continued)

(58) Field of Classification Search
CPC .... B41F 5/24; B41F 5/10; B41F 27/14; B41F 30/02; B41F 13/08; B41F 31/26;
(Continued)

(56) References Cited

U.S. PATENT DOCUMENTS 562,567 A 6/1896 Bramble
1,733,707 A * 10/1929 Wood ............... B41F 13/21
101/220

(Continued)

FOREIGN PATENT DOCUMENTS

CL 200902121 11/2009
CN 101479107 A 7/2009
(Continued)

OTHER PUBLICATIONS

National Intellectual Property Administration (CNIPA) of the People's Republic of China, Office Action issued in CN 201880091979.4, dated May 31, 2021 with English language translation, 21 pages.
(Continued)

*Primary Examiner* — Daniel J Colilla
(74) *Attorney, Agent, or Firm* — CANTOR COLBURN LLP

(57) ABSTRACT

A flexographic printing device and a method are provided for simultaneously printing at least two material webs having different thicknesses in the printing device. The flexographic printing device includes a printing unit having a printing roller carrying on a surface thereof an image to be printed, an impression roller and an anilox roller adapted to feed printing ink from a printing ink chamber onto a printing cliché mounted on the printing roller. The printing unit is configured for simultaneously printing the material webs having different thicknesses, by adjusting the radial exten-
(Continued)

sion of the surface of the printing roller, impression cylinder and/or anilox roller to be adapted to the respective material web to be printed.

19 Claims, 7 Drawing Sheets

(51) Int. Cl.
  *B41F 13/18* (2006.01)
  *B41M 1/04* (2006.01)
  *B41N 7/06* (2006.01)
  *A61F 13/84* (2006.01)
  *B41N 7/04* (2006.01)
(52) U.S. Cl.
  CPC .............. *B41M 1/04* (2013.01); *B41N 7/04* (2013.01); *B41N 7/06* (2013.01); *A61F 2013/8497* (2013.01)
(58) Field of Classification Search
  CPC ......... B41F 17/38; B41F 17/003; B41M 1/04; B41M 1/26; B41N 1/06; B41N 7/06; B41P 2227/11
  See application file for complete search history.

(56) References Cited

U.S. PATENT DOCUMENTS

| | | | | |
|---|---|---|---|---|
| 1,763,679 A * | 6/1930 | Stickney | ............... | B41F 5/04 101/224 |
| 3,138,097 A * | 6/1964 | Harris | .................. | B41F 31/18 101/216 |
| 4,008,661 A * | 2/1977 | Mathis | .................. | B41F 13/02 101/181 |
| 4,309,945 A | 1/1982 | Marion | | |
| 5,345,864 A | 9/1994 | Machguth et al. | | |
| 5,636,567 A | 6/1997 | Mucha et al. | | |
| 5,894,799 A | 4/1999 | Bart et al. | | |
| 7,367,264 B2 | 5/2008 | Beaudry | | |
| 2002/0002920 A1 | 1/2002 | Dilling et al. | | |
| 2007/0144391 A1* | 6/2007 | Kuckelmann | ............ | B41M 1/00 101/485 |
| 2007/0289469 A1* | 12/2007 | Roland | ................ | B41F 27/105 101/477 |
| 2009/0211475 A1 | 8/2009 | Taylor | | |
| 2010/0089264 A1 | 4/2010 | Warner | | |
| 2010/0129620 A1 | 5/2010 | Lopez-Mas et al. | | |
| 2011/0046591 A1 | 2/2011 | Warner | | |
| 2011/0120328 A1* | 5/2011 | Van Den Brink | ...... | B41F 13/44 101/176 |
| 2013/0025478 A1* | 1/2013 | Demand | ................ | B44B 5/028 101/3.1 |
| 2013/0260070 A1 | 10/2013 | Alter et al. | | |
| 2015/0112293 A1 | 4/2015 | Gust et al. | | |
| 2016/0159071 A1 | 6/2016 | Ludin | | |

FOREIGN PATENT DOCUMENTS

| | | | |
|---|---|---|---|
| CN | 204184028 | U | 3/2015 |
| CN | 204566874 | U | 8/2015 |
| CN | 105252902 | A | 1/2016 |
| CN | 106573464 | A | 4/2017 |
| CO | 6341586 | A2 | 11/2011 |
| CO | 7000762 | A2 | 7/2014 |
| DE | 102004056389 | A1 | 4/2006 |
| EP | 0051037 | A1 | 5/1982 |
| EP | 1927469 | A2 | 6/2008 |
| EP | 3774342 | A4 | 10/2021 |
| ES | 8801885 | A2 | 3/1988 |
| ES | 2086778 | T3 | 7/1996 |
| FR | 2656831 | A1 | 7/1991 |
| JP | 2008087481 | A | 4/2008 |
| JP | 2016064016 | A | 4/2016 |
| WO | 2007069965 | A1 | 6/2007 |
| WO | 2017134082 | A1 | 8/2017 |

OTHER PUBLICATIONS

Federal Service for Intellectual Property, Russia, Decision to Grant issued in Application No. 2020135523/28(065453), dated Apr. 20, 2021 with English language translation, 22 pages.
Japanese Patent Office, Office Action issued in Application No. 2020-554149, dated Oct. 15, 2021 with English language translation, 8 pages.
Australian Government, IP Australia, Examination report No. 1 for standard patent application issued in corresponding Australian Application No. 2017428325, dated Aug. 6, 2020, 5 pages.
Federal Service for Intellectual Property, Russia, Official Action and Search Report issued in corresponding Russian Patent Application No. 2020111224/03(018874), dated Aug. 11, 2020, 13 pages, with English Translation.
Australian Government, IP Australia, Examination report No. 1 for standard patent application issued in Australian Patent Application No. 2017428323, dated Aug. 4, 2020, 4 pages.
Federal Service for Intellectual Property, Russia, Official Notification of examination results and Search Report issued in Application No. 2020111223(018873), dated Aug. 11, 2020, 11 pages, with English translation.
Pinzon Pinzon & Asociados, Third Party Submission in Application No. NC2020/0001993 dated May 5, 2019, 19 pages (no English translation available).
International Search Authority, Search Report and Written Opinion issued in PCT/SE2018/050357 dated Nov. 23, 2018 (16 pages).
National Intellectual Property Administration of the People's Republic of China, 2nd Office Action issued in Application No. 201880091979. 4, dated Jan. 20, 2022 with English language translation, 21 pages.
Colombian Office Action; Colombian Application No. NC2020/0012625; dated May 25, 2022; 18 pages.
Colombian Office Action and Search Report; Colombian Application No. 2020/0012625; Report dated Sep. 28, 2022; With Translation (pp. 1-26).
Brazilian Search Report and Written Opinion for Brazilian Application No. BR112020020062-0; Report dated Jul. 21, 2022 (pp. 1-4).

* cited by examiner

FLEXOGRAPHIC PRINTING DEVICE AND A METHOD OF SIMULTANEOUSLY PRINTING AT LEAST TWO MATERIAL WEBS HAVING DIFFERENT THICKNESSES

CROSS-REFERENCE TO RELATED APPLICATION

This application is a national phase entry of, and claims priority to, International Application No. PCT/SE2018/050357, filed Apr. 5, 2018. The above-mentioned patent application is incorporated herein by reference in its entirety.

TECHNICAL FIELD

This application relates to a flexographic printing device and a method of simultaneously printing at least two material webs.

BACKGROUND

Absorbent articles for absorption of body fluids are available in a number of different designs. For absorption of urine and excrement, use is generally made of diapers or incontinence guards with a shape which, during use, simulates a pair of briefs. There are other types of absorbent articles, such as feminine hygiene products. These products typically include a topsheet facing the body of the user, a backsheet facing the garment of a user, and an absorbent layer sandwiched between the inner, topsheet and outer, backsheet. To increase the aesthetics and functionality of the particular article, graphics may be printed on various portions of the article. The absorbent articles may comprise further structural elements adapted to improve the fit of the articles to the body of the user or to improve leakage protection. For example, the absorbent articles may comprise side panels and some known hygiene articles, such as diapers which can be both open-type and pant-type, are provided with liquid side barriers along the longitudinal edges of the absorbent core which are intended to reduce the risk of side-edge leakage. To increase the aesthetic appearance and functionality of the particular article, different types printing patterns may be printed on various portions of the article.

The topsheet and backsheet of the absorbent article may be made from a nonwoven material. Printing is typically applied to the particular nonwoven layer prior to attaching it to the other layers of the absorbent article. One example of printing is by way of a flexographic printing press machine, e.g., as shown by US Patent Publication No. 2010/0129620. In a typical printing configuration, a master roll of nonwoven material is fed between a print roller and an impression roller. Adjacent to the print roller is an anilox roller, which feeds ink from the ink cavity onto the print roller. Upon rotation of the anilox roller and print roller, ink is transferred to the print roller. Depending on the design of the print roller, a particular graphic is printed onto the nonwoven material when it is fed between the print roller and anilox roller.

The nonwoven materials used in the topsheet and side panels of an absorbent product may have different thicknesses. To handle materials with different thicknesses in printing processes is difficult, e.g., since the nip pressure in the printing unit between a printing roller and the compression roller will be different.

To print materials with different thicknesses inline in the existing manufacturing processes has been challenging and therefore, the side panel materials have often been pre-printed while the topsheet material is printed in-line with the manufacturing process. However, the manufacturing process is thus dependent on the delivery of the pre-printed material. Also, it may be difficult to optimize the exact amount of the pre-printed material, whereby the production process may suffer from insufficient amount of pre-printed material or high costs are involved if too much of the pre-printed material is ordered.

To be able to print substrates having different thicknesses has been challenging. In the prior art there are solutions which relate to making adjustments in the printing equipment when there are variations in the printing device components e.g., as shown in U.S. Pat. No. 5,894,799. However, the cushion element is not configured to compensate for variation in the thicknesses of the material to be printed. Therefore, there is a desire to perform the printing of both the topsheet and the side panels in a single process in a simple way, while the quality of the printed product is maintained. To this end, it would be desirable to improve printing devices and methods in such a technical context to overcome the deficiencies in the known art.

SUMMARY

In order to achieve these technical objectives, there is provided a one-step printing process in which printing substrates having different thicknesses can be printed simultaneously according to embodiments of the present invention. Also, it is an objective to enable a printing process in-line with the manufacturing process of an absorbent article.

Another objective is to provide a cost efficient printing process which can be used in the existing manufacturing process without a need to increase the amount of printing units.

It is also an objective to provide for better control of the manufacturing process such that the supply of for the printed material corresponds to the need of the printed material.

Further, it is an objective to improve the flexibility of the printing process, and thus for example to obtain a method which enables a more easy change of printing pattern.

The objectives above are attained by a flexographic printing device including a printing unit having a printing roller carrying on a surface thereof an image to be printed, an impression roller and an anilox roller adapted to feed printing ink from a printing ink chamber onto the printing roller. The printing unit is configured for simultaneously printing at least two material webs having different thicknesses, the material webs being printed when they pass a printing nip formed between the printing roller and the impression roller. The printing device is further characterized by one or more of the following:

I. the radial extension of the surface carrying the image to be printed of the printing roller, is adapted in respect to the thickness of the respective material web to be printed; and/or II. the radial extension of the surface of the impression roller is adapted in respect to the thickness of the material webs to be printed; and/or III. the radial extension of the anilox roller is adapted in respect to the thickness of the material web to be printed.

By configuring the printing unit according to any one or any combination of the alternatives I, II, and III above, only a simple structural adaptation of the printing unit is required while printing of two material webs having different thicknesses is provided. Also, the printing device described herein will not deteriorate the web materials, which may be of nonwoven type. Also, an even printing quality on all material webs will be obtained.

The image to be printed may be provided as a cliché mounted on the printing roller. The printing roller may contain an equal amount of clichés as there are material webs. The cliché or clichés may have a radial extension adapted to the thickness of the respective material web to be printed. In this way, it is possible to provide a suitable printing cliché for the material in question, and the configuration of the printing device is simple. Alternatively, the image to be printed may be provided as an engraved printing sleeve or as an engraved printing roller.

Alternatively or additionally, the surface of the impression roller may have an equal amount of surface zones as there are material webs. The zones may have a radial extension adapted to the thickness of the respective material web to be printed. The zone or zones of the impression roller may comprise a cover having a radial extension adapted to the thickness of the respective material web to be printed. In this way, an easy configuration of the printing device can be made if needed. This allows also for quick adaptation of the printing unit. Also, the clichés may be prepared in a standard manner and have same dimensions, or a single cliché for printing different webs may be used.

In an alternative variant, the anilox roller may be axially inclined to adapt the radial extension of the anilox roller to the thickness of the respective material web to be printed. In this way, more printing ink may be provided to the printing roller in a controlled manner.

Alternatively or additionally, the printing unit may comprise an equal amount of anilox rollers as there are material webs. Each of the anilox rollers may have a radial extension adapted to the thickness of the respective material web to be printed. Alternatively or additionally, the radial position of each of the anilox rollers may be adapted to the thickness of the respective material web to be printed. By this configuration, the delivery of the printing ink from the printing ink chamber to the printing roller may be controlled in a desired way.

The printing device may further include at least one feeding device for the at least two material webs. The feeding device may include one or several master rolls, i.e. storage rolls for the material webs to be printed. In this way, the feeding system is flexible and the materials can be printed as separate or combined material webs.

In another embodiment, a method is provided of simultaneously printing at least two material webs having different thicknesses in a printing device. The method includes a step of adapting the printing unit by arranging:
 I. the radial extension of the surface of the printing roller carrying the image to be printed such that it is adapted in respect to the thickness of the material web to be printed; and/or
 II. the surface of the impression roller such that the radial extension along the surface of the impression roller is adapted to the thickness of the material webs to be printed; and/or
 III. the surface of the anilox roller such that the radial extension along the surface of the anilox roller is adapted to the thickness of the material web to be printed by arranging a respective anilox roller to the respective material web and/or by axially inclining the anilox roller.

By the method, it is possible to adapt a printing device to print materials of different thicknesses in one process. Also, materials suitable for use in absorbent articles, which often are sensitive and have elastic properties or properties that make the materials rather soft than strong and dimensionally stable, can be printed with the printing device as arranged by the present method.

In the method, the image to be printed may be provided in the form of at least one printing cliché, an engraved printing sleeve or as an engraved printing roller comprising an equal amount of printing pattern zones as the amount of the material webs to be printed. Alternatively, the image to be printed may be provided as printing clichés, the amount of printing clichés corresponding to the amount of the material webs, and wherein each printing cliché is configured to print on the respective material web. The configuration of the printing clichés may be done as described above by adapting the radial extension of the respective cliché to the respective material web. Thus, the printing unit can be configured to the different thicknesses of the material webs in a simple way.

The method may further include simultaneously feeding the material webs to the printing unit and printing a respective printing pattern on the respective webs. Thus, the material webs can be simultaneously printed. The material webs may be separate webs, and the method may include feeding the webs from separate feeding devices. Thus, the material webs can be printed without pre-processing the webs before printing, e.g., by attaching the webs together or by winding the webs to a common roll. Alternatively, the material webs may be connected to each other in a parallel manner, such as by welding or gluing, and the method includes feeding the webs from a common feeding device. Thus, the method allows for printing the material webs in a flexible way.

The method may include printing on two material webs. Alternatively three material webs having at least two different thicknesses may be printed by the method. The amount of webs may be higher. The printing roller may include a printing cliché for the respective material web. The method thus allows for printing several webs simultaneously. The material webs may be connected to each other in a parallel manner, such as by welding or gluing, and the method may comprise feeding the webs from a common feeding device. For example, there may be three separate material webs and the method may include feeding the webs from separate feeding devices. Further, the three material webs may be connected to each other in a parallel manner, such as by welding or gluing. The method may include feeding the webs from a common feeding device. Thus, the feeding of the material webs may be done in a flexible way. In a variant, the method may include printing on three material webs, where two of the three material webs may have the same thickness and one of the webs is thicker or thinner than the two having the same thickness.

In the method, the printing patterns provided by the clichés may be different from each other, whereby printed material webs having different purposes may be provided in a single printing process.

In yet another embodiment, a material web is provided and is printed by the method as defined above. The adaptation of the printing unit may affect the printed images in such a way that for example, when the material webs are attached to each other, the printing quality is very similar to each other in the material webs compared to material webs printed in a printing unit which is not adapted for printing material webs with different thicknesses. Also, by the present method the material for the material webs can be a nonwoven, a plastic film, a woven material, a laminate or a combination thereof.

The present disclosure also relates to the use of the printed material web or webs in a hygiene absorbent article comprising a topsheet, backsheet, an absorbent core between the topsheet and the backsheet, and optionally side panels, leg elastics, waist elastics and/or a belt. The printed material can be used in at least one of or all the parts of such absorbent article.

Further features and advantages of the various embodiments are described in more detail below in the detailed description.

BRIEF DESCRIPTION OF THE DRAWINGS

The features and advantages of the invention will be appreciated upon reference to the following drawings. The accompanying drawings, which are incorporated in and constitute a part of this specification, illustrate one or more embodiments of the invention and, together with the general description given above and the detailed description given below, explain the one or more embodiments of the invention.

FIG. 1b is a cross sectional view of the diaper in FIG. 1a.

DETAILED DESCRIPTION

According to the present application, at least two material webs having different thicknesses are simultaneously printed in a common printing unit of a printing device. The material webs are usable in absorbent articles. By "thickness" is meant a measure of the material dimension in a plane perpendicular to the plane of the extension of the machine direction and cross direction of the material web, herein also referred to as a Z-direction. In case the material is compressible, the thickness and the average density of the material may be measured at a pressure of 0.5 kPa as defined below.

A pressure of 0.5 kPa is applied to the nonwoven material via a foot which is smaller than the area of the sample. The foot is placed inside the area to be measured. The thickness of the sample is measured while subject to this pressure. The samples for which densities are to be calculated are cut out from the sample, and the surface weight ($g/cm^2$) of these samples is calculated from their mass/surface area. From the surface weight and the thickness, the average density of these areas is calculated. The average density ($kg/m^3$) is calculated by dividing the surface weight by the thickness.

An absorbent article or garment as understood in the present application is defined as an article or garment used for the absorption of body fluids, including but not limited to, infant diapers and training pants, adult incontinence products, feminine hygiene products such as sanitary napkins and panty liners, gender specific absorbent products, and pet training absorbent articles. The absorbent articles of the mentioned type may also be referred to as wearable absorbent articles. The absorbent articles usually comprise a liquid permeable topsheet, a liquid impermeable backsheet and an absorbent core sandwiched there between. However, an absorbent article may also include other types of products, such as household, medical products, or the like.

Figure 1A:
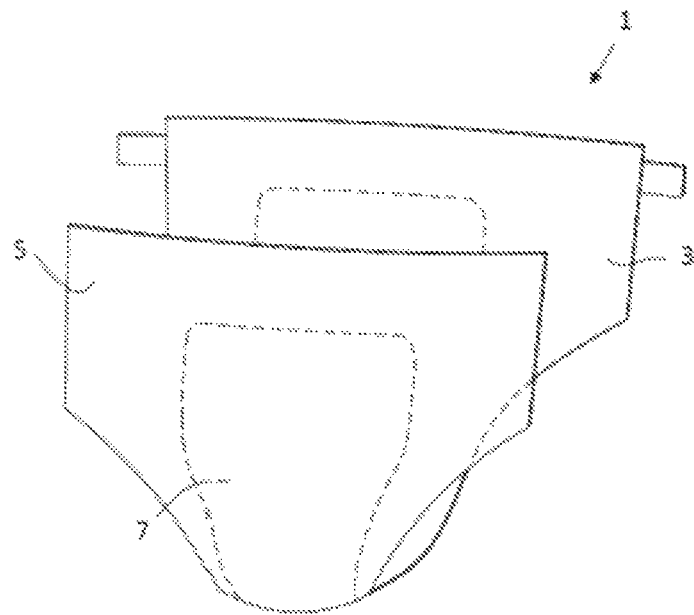
FIG. 1a is a side view of an open diaper as an example of an absorbent article.
Figure 1B:
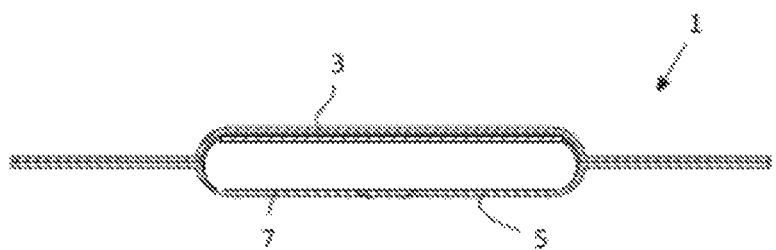

An example of a wearable absorbent article 1, in which the printed material webs of the present disclosure can be used, is shown in FIGS. 1a and 1n cross section in FIG. 1b. The example shown is in the form of an open diaper 1. However, other types of absorbent articles could be the above-mentioned types, e.g., pant-type diapers, sanitary napkins, panty liners, and incontinence protection articles such as incontinence pads. Also, the absorbent article could be a wound care product (not shown). The absorbent article 1 typically comprises a liquid-permeable topsheet 3, a backsheet 5 and an absorbent body 7 enclosed between the liquid-permeable topsheet 3 and the backsheet 5. The liquid permeable topsheet 3 faces the wearer's body during use and is arranged to absorb body liquids such as urine and blood. The material of the topsheet 3 may comprise a nonwoven material of spunbond type, a meltblown material etc, and may be comprise several types of materials. The topsheet may comprise topsheet materials having different thicknesses. The backsheet 5 is typically liquid-impermeable, optionally breathable and may comprise a plastic (e.g., polyolefin) film, a plastic coated nonwoven or a hydrophobic nonwoven, and may also comprise a combination of different materials, which may have different thicknesses. Any one of the topsheet, backsheet and the core may comprise a printed image or pattern, and may thus be printed by the printing device or by using the printing method of the present disclosure.

The absorbent body 7 acts to receive and contain liquid and other bodily exudates. The absorbent article contains absorbent materials. Examples of commonly occurring absorbent materials are cellulosic fluff pulp, tissue layers, superabsorbent polymers, absorbent foam materials, absorbent nonwoven materials or the like. The absorbent body 7 may be constructed from several layers, such as a liquid acquisition or distribution layer or a storage layer in order to fulfil functions which are desired for an absorbent body; i.e. capacity to quickly receive liquid, distribute it within the body and store it. The layers of the absorbent body are designed to receive a large amount of liquid in a short time and distribute it evenly across the absorbent body. The size and absorbent capacity of the absorbent body may be varied to be suited for different uses such as for baby diapers, sanitary napkins and incontinence pads.

Various parts of the absorbent article may include a printed image or pattern, such as the backsheet, topsheet and the core. Wearable absorbent articles may comprise further parts to improve the fit or to assist the attachment of the article to the user, such as wings, leg cuffs, waist elastics or a waist portion, a fastening system, a landing zone, side panels, handles, fastening tabs, a pocket, spacers, or combinations thereof (not shown). Each of these parts may include a printed image or pattern.

Thus, the material webs to be printed according to the present disclosure includes various types of materials, such as nonwoven materials and plastic films, such as plastic films of PE (polyethylene) or PP (polypropylene), PET (polyethylene terephthalate), PLA (polylactic acid) and/or amyl, or, for that matter, any other thermoplastic polymer, or a mixture or copolymers of the aforementioned polymers. The material web may also be a laminate comprising at least two or more material layers of the above-mentioned type.

The term "nonwoven material" refers to a primarily fibrous assembly, which has structural integrity obtained by mechanical interlocking or by fusing fibers or by bonding by a cementing medium, such as starch the fibers. Thus, no weaving and/or knitting are/is involved. Also, the nonwoven is other than a traditional paper, woven, or knit. Nonwoven materials can be produced from the binding of natural and/or synthetic fibers, and are materials such as spun-bonded, SMS (spun bond, melt blown spun bond), SSMS, SMMS, carded, hydroentangled, spun laced, ultrasonically welded, as well as nonwovens made out of nanofibers, polypropylene tow, spunmelt highloft and the like. The nonwoven material may be also an air laid material, meaning that a web of separated fibers or staple fibers is produced by laying the fibres on a wire and by forming a web in the presence of an airstream. The web may be bonded by using thermal resins. However, other types of nonwoven material may be included, particularly those that may be applied as an inner or outer layer of an absorbent article or garment. For example, the grammage of the nonwoven material is in the range of 1-100 gsm (grams per square meter). However, this range may be more or less, depending on application and design preference. The material web may consist or comprise of other materials present in an absorbent article.

According to a variant, the material web to be printed may be a spunlace, also referred to as spunbond, nonwoven material. A spunlace nonwoven product is derived from a process of entangling a web of loose fibres through multiple rows of jets of water at high pressure; this process entangles the fabrics and interlinks the fibres. There are several terms for spunlace nonwoven fabric or spunlaced, such as jet entangled, needled, hydroenentangled or hydraulic, but the term spunlace or spunlaced is the most popular in the nonwoven industry. The raw material for spunlace web material can be polypropylene (PP), polyethylene (PE) polyester (PET), polyamide (PA), cellulosic fibres or a combination of these and different weights and compositions are possible, such as viscose, polyester, cotton, nylon and microfiber, wherein viscose is the most commonly used raw material. Thus, if a combination of different fibres is used, this can be a mixture of fibres from different polymers, although each fibre can also include different polymers (e.g., PP/PE bi-component fibres or PP/PE copolymers). The spunlace material usually comprises polypropylene or polyethylene fibres which provide for optimal comfort for the nonwoven material. Other suitable fibres for making the nonwoven material are for example natural fibres such as bamboo, cotton and flax. The grammage of the spunlace nonwoven material can be typically from 25-120 gsm or from 40-90 gsm. The thickness of the material may vary of from 0.1 to 3 mm, such as 0.3 to 2.5 mm.

One type of the material web to be printed may be high loft nonwoven, which may be a spunmelt nonwoven. Spunmelt is a generic term describing the manufacturing of nonwoven webs directly from thermoplastic polymers. It encompasses two processes and the combination of both: spunlaid (also known as spunbond) nonwoven and meltblown nonwoven. In a spunlaid process, polymer granules are melted and molten polymer is extruded through spinnerets. The continuous filaments are cooled and deposited on to a conveyor to form a uniform web. Some remaining temperature can cause filaments to adhere to one another, but this cannot be regarded as the principal method of bonding. The spunlaid process has the advantage of giving nonwovens greater strength, but raw material flexibility is more restricted. Co-extrusion of second components is used in several spunlaid processes, usually to provide extra properties or bonding capabilities. In meltblown web formation, low viscosity polymers are extruded into a high velocity airstream on leaving the spinneret. This scatters the melt, solidifies it and breaks it up into a fibrous web. The liquid acquisition sheet material may be of a spunbonded material and may be a spunbond-meltbond-spunbond (SMS) material. The high loft nonwoven layer may have a thickness ranging from 0.3 mm to 4.0 mm, for example 1.0 mm as measured at a pressure of 0.5 kPa (according to the test method described further below). The grammage, i.e. basis weight of the high loft material may for example range from 15 gsm to 500 gsm, in particular from 30 gsm to 200 gsm, such as 30-90 gsm, for example 64 gsm.

The material web to be printed may further be a carded nonwoven, which can be produced by air laid process after fibers have been separated and aligned. The carded web can be bonded by one or more technologies used in connection with air laid technology to provide integrity for the fabric. Further, the material web can be an air laid nonwoven which can be produced with fluff or wood pulp. The fluff fibres are dispersed into a fast mowing air stream and condensed onto a moving screen by pressure and vacuum. The web can be bonded with resin and/or thermal plastic resin dispersed within the pulp. The web can be thermo-bonded (by heat), latex bonded (with adhesive) or multibonded (a combination of thermo and latex bonding) or mechanically bonded (high compression and temperature, bonding by hydrogen). The grammage of the air laid nonwoven can suitably be from 30-150 gsm or from 50 to 100 gsm. The thickness of the web can vary from 0.1 to 3 mm, such as from 0.5 to 2.5 mm.

The material web to be printed may be aimed for use as a topsheet material, which normally lies in direct contact with the wearer's body. The topsheet material is preferably soft, comfortable and liquid-permeable. The topsheet can comprise any of the nonwoven materials discussed above and may be a combination of several types of material webs which are placed in different parts of the topsheet. Further examples of topsheet materials are porous foams, apertured plastic films etc. The topsheet may comprise different materials having different thicknesses. The present printing device comprising a printing unit configured for simultaneously printing at least two material webs having different thicknesses can be used for printing the topsheet material which has different thicknesses in different parts of the absorbent article.

The backsheet lies in contact with the wearer's garments, and is liquid-impermeable. The backsheet refers to the liquid impervious material forming the outer cover of the absorbent article. The backsheet can comprise a thin plastic film, e.g., a polyethylene or polypropylene film, a nonwoven material coated with a liquid impervious material, a hydrophobic nonwoven material, which resists liquid penetration, or a laminate of a plastic film and a nonwoven material. Other laminate materials which are suitable for use as the backsheet are laminates of a nonwoven material and high loft material. The backsheet material may be breathable so as to allow vapor to escape from the absorbent core, while still preventing liquids from passing there through. Examples of breathable backsheet materials are porous polymeric films, nonwoven laminates of spunbond and meltblown layers and laminates of porous polymeric films and nonwoven materials. In one embodiment, the backsheet comprises nonwoven material in at least the garment-facing surface thereof. The backsheet material may also comprise different materials having different thicknesses. The present printing device comprising a printing unit configured for simultaneously printing at least two material webs having different thicknesses can be used for printing the backsheet material which has different thicknesses in different parts of the absorbent article.

Figure 2:
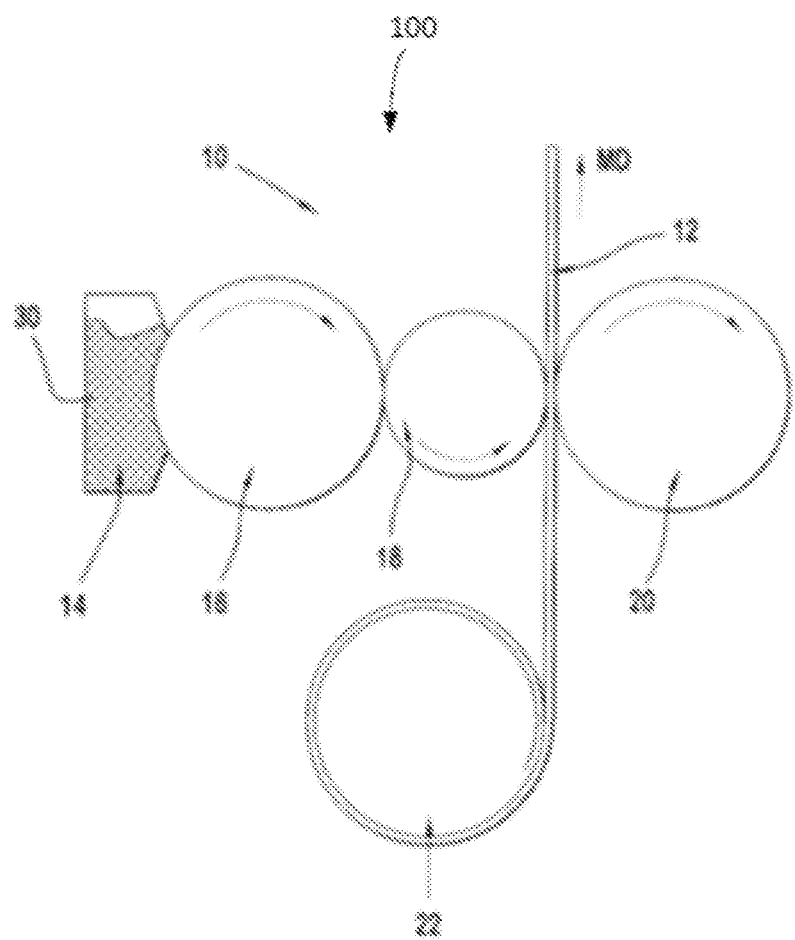
FIG. 2 is a schematic side view of a flexographic printing unit.

With reference to FIG. 2, an example of a flexographic printing device 10 for printing on a continuous web of nonwoven material 12 is schematically shown in a side view. The device includes one printing unit 100, which includes a printing ink chamber 14, an anilox roller 16, a printing roller 18, and an impression roller 20. It should be noted that the printing device 10 may include several printing units, for example if multi-color printed designs are to be provided on the printing materials. In the FIG. 1 only one web of nonwoven material can be seen in the side view, but as is clear, the printing device of the present disclosure is configured to print at least two material webs having different thicknesses. The webs are fed between a printing roller 18 and an impression roller 20 from a master roll 22, which is a storage roll, for a nonwoven material. The material web is fed in a machine direction (MD). The material webs are printed when the webs pass a printing nip formed between the printing roller, on which a printing cliché is mounted, and the impression roller.

By cliché, which is also referred to as cliché or flexographic (flexo) printing plate, is in this disclosure meant a substrate, a plate of polymeric rubber type or plastic material sheet, such as photopolymeric material, or an engraved metallic plate, which carriers the image to be printed. The image to be printed may also be provided an engraved printing sleeve or as an engraved printing roller. The plate used may have the image areas raised above the non-image areas. The thickness of the cliché may be for example within 0.5 to 4 mm, but is not limited thereto. The cliché is mounted on a printing roller and therefore the thicker the cliché is, the larger the radial extension of the cliché will be. The amount of clichés mounted on the printing roller can be varied, but at least one printing cliché is used to print one or several material webs. The cliché may have substantially the same radial extension over the whole area of the cliché. Alternatively, and according to a variant of the present invention, the thickness of the cliché and thus the radial extension of the cliché when mounted on the printing cylinder, is adapted to the thickness of the material web to be printed. In case of only one printing cliché, the cliché may have areas of different thicknesses adapted to the thickness of the material web to be printed. Alternatively, there may be a dedicated cliché for each respective material web to be printed, and each of the clichés may have a thickness adapted to the thickness of the material web to be printed.

Each of the nonwoven material webs may comprise multiple layers of material and they may be fed from a feeding device. The feeding device may comprise at least one master roll, i.e. a storage roll containing the material web or webs to be printed, for the at least two material webs. The at least two material webs having different thicknesses may be attached to each other in a parallel manner in machine direction prior to the printing process, and thus the webs may be fed from a common master roll 22. However, the feeding device may comprise a respective master roll 22 for each of the material webs to be printed.

In general, the anilox roller 16 rotates in a clockwise (CW) direction and carriers ink 30 from the printing ink chamber 14 to the printing roller 18. The printing roller 18 is disposed adjacent to the anilox roller 16 and rotates in an counterclockwise direction (CCW). Ink 30 from the anilox roller 16 is transferred to protruding graphic design portions on a printing cliché on the outer circumference of the printing roller 18. The printing cliché mounted on the printing roller 18 may include a removable sleeve, printing plate, or the like, for containing the particular design.

The impression roller 20, which rotates in a clockwise (CW) direction, is disposed adjacent to the printing roller 18 and on the opposite side of the material web 12, such that the cliché on the printing roller 18 is pressed against and printed on the material web 12. However, it should be understood that the rollers may rotate in the opposite direction, so long as the rollers are appropriately coordinated.

Figure 3:
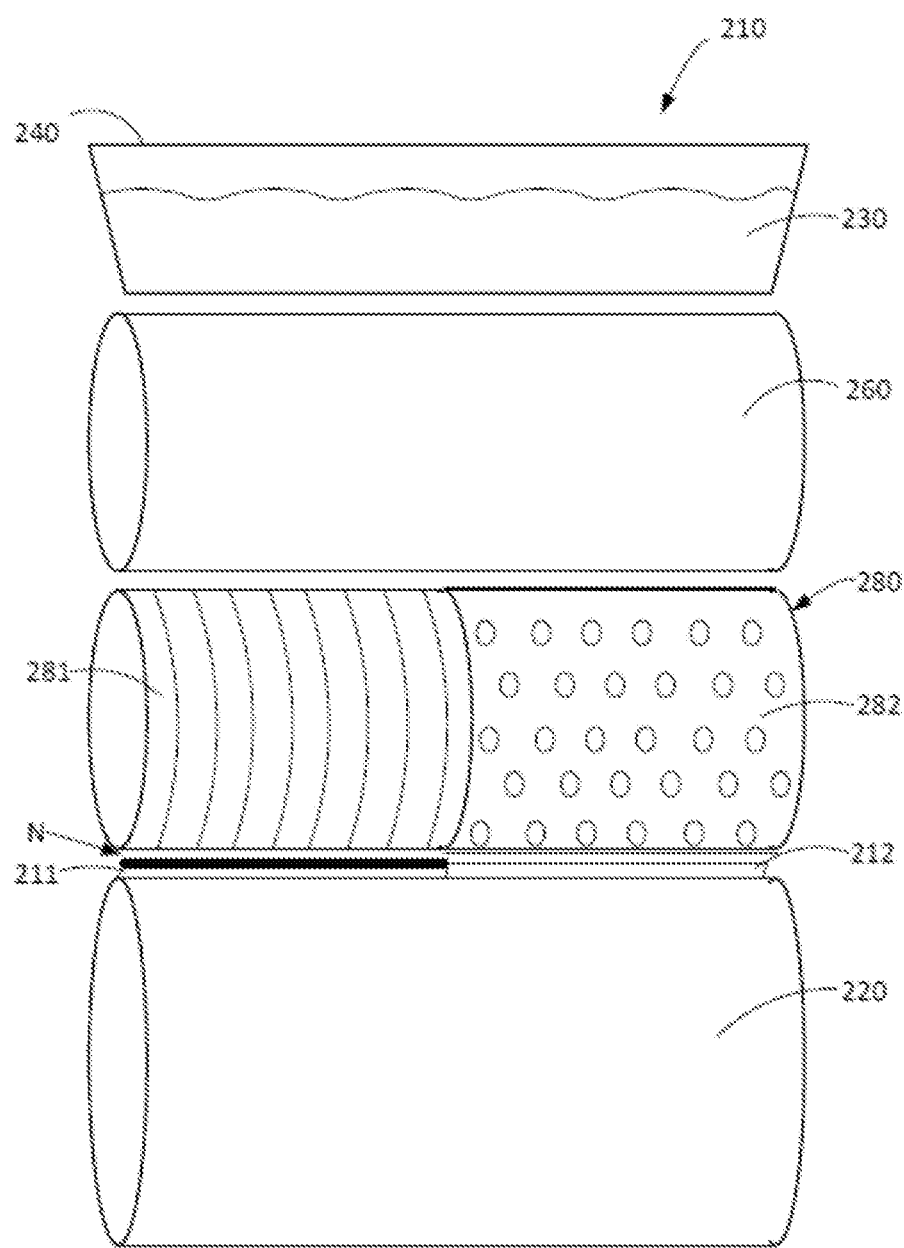
FIG. 3 is a schematic front view of a flexographic printing unit according to one embodiment.

With reference to FIG. 3 an example of a flexographic printing unit 210 in a flexographic printing device according to the present disclosure is schematically shown. The printing unit 210 comprises a printing ink chamber 240 for a printing ink 230, an anilox roller 260, which transfers the printing ink to the printing roller 280 comprising two printing clichés 281 and 282 and an impression roller 220, which presses towards the printing roller 280 during printing. The printing unit is configured for simultaneously printing at least two material webs 211, 212 having different thicknesses. The first material web 211 is thicker than the second material web 212. In the illustrated example, the radial extension of the at least one cliché 282, when mounted on the printing roller 280, is adapted in respect to the thickness of the thinner second material web 212 to be printed. More specifically, the printing roller 280 contains an equal amount of clichés and material webs, i.e. two clichés 281 and 282, and two material webs 211 and 212. The clichés 281 and 282 have a radial extension adapted to the thickness of the respective material web to be printed, and thus the second cliché 282 and therefore has a larger radial extension than the first cliché 281. Suitably, the larger radial extension may be provided by providing clichés having different thicknesses in a way corresponding to the different thicknesses of the material webs. The material of the thicker cliché may be more flexible than the thinner cliché, whereby it can be pressed more towards an anilox roller 260 than the thinner cliché. The anilox roller provides a printing ink 230 from a printing ink chamber 240 to the printing roller 280 and the clichés thereof. Alternatively or additionally, to obtain larger radial extension, a further material layer can be provided between a printing roller and a cliché. In FIG. 3 this would mean that a further material layer is provided between the printing roller 280 and the second cliché 282 adapted to print on the thinner second material web 212. The thinner the material web is, the larger the radial extension of the cliché can be arranged. For example, if the first material has a thickness of 1 mm and the second material is 10% thinner, i.e. 0.9 mm, the second cliché should compensate for the thickness difference of 0.1 mm in a corresponding way. In this way, the distance between the second material web 212 and the second cliché 282 will be close to the same as the distance between the first material web 211 and the second cliché 282. Also, since the material webs are printed when they pass a printing nip (N) formed between the printing cliché mounted on the printing roller and the impression roller, the nip pressure will be more equal along the axial extension of the printing roller than in case the clichés had a same radial extension. By axial extension is meant the extension in a direction of the center axis of a roller, which has a substantially circular cylindrical shape. In the illustrated drawings, the axial extension is in the horizontal direction. In this way, the process control and resulting printing quality may be improved.

Figure 4:
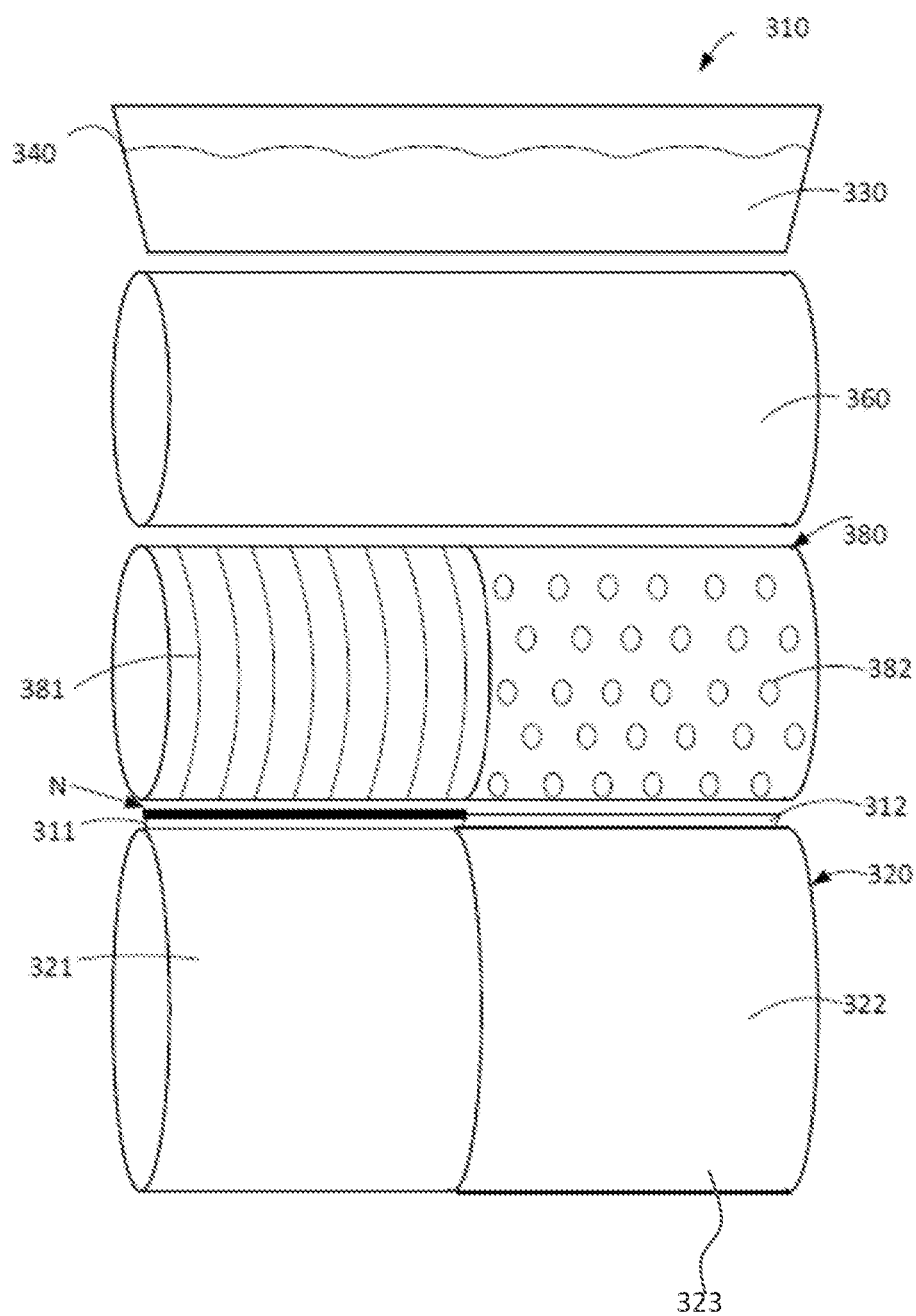
FIG. 4 is a schematic front view of a flexographic printing unit according to another embodiment.

According to another variant of the present disclosure, the radial extension of the surface of the impression roller can be additionally or alternatively to the example described above be adapted in respect to the thickness of the material webs to be printed. FIG. 4 shows schematically an arrangement of such printing unit 310 in a flexographic printing device comprising a printing unit configured for simultaneously printing at least two material webs 311, 312 having different thicknesses. The printing unit 310 comprises a printing ink chamber 340 for a printing ink 330, an anilox roller 360, which transfers the printing ink to the printing roller 380 comprising two printing clichés 381 and 382. Alternatively only one large printing cliché with two separate printing patterns could be used instead. The first material web 311 is thicker than the second material web 312. The printing unit comprises an impression roller 320 having two surface zones, a first surface zone 321 and a second surface zone 322, i.e. an equal amount of zones as there are material webs 311 and 312. The surface zones 321 and 322 have a radial extension adapted to the thickness of the respective material web 311 and 312 to be printed. In the illustrated example, the radial extension of the second surface zone 322 of the impression roller 320 is adapted in respect to the thickness of the thinner second material web 312 to be printed. More specifically, surface zones 321 and 322 have a radial extension adapted to the thickness of the respective material web to be printed, and thus the second surface zone 322 has a larger radial extension than the first surface zone 321. Suitably, the larger radial extension may be provided by providing a cover 323 to the impression cylinder 320. The cover 323 may be an elastic sheet, e.g., rubber sheet or a metallic sheet or folio. By providing such cover, an easy and quick configuration of the printing unit to the different material thicknesses can be obtained. Alternatively or additionally, a cover in the form of a cushion may be provided under a surface cover material of the impression cylinder 320. In this way a simple configuration of the printing unit can be made in a more permanent way, i.e. the cushion needs not to be changed in between different printing runs, if material webs with the same thickness difference are to be printed also in the next run. The thinner the material web to be printed is, the larger the radial extension of the zone of the impression cylinder needs to be. The larger radial extension can be provided by providing a thicker cover 323 over the zone adapted to print on the thinner material. For example, if the second material is 10% thinner than the first material web, the second surface zone should compensate for the thickness difference in a corresponding way. In this way, the distance between the second material web 312 and a cliché 382 mounted on the printing roller 380 is close to the same as the distance between the first material web 311 and the second cliché 381, when the impression cylinder 320 presses the webs 311 and 312 towards the printing roller 380 during the printing process. Thus, when the material webs are printed when they pass a printing nip (N) formed between the printing cliché mounted on the printing roller and the impression roller, the nip pressure will be more equal along the axial extension of the printing roller than in a case where the surface of the impression cylinder 320 had a same radial extension. In this way, the process control and resulting printing quality may be maintained at a same level as if the material webs had the same thickness.

Figure 5:
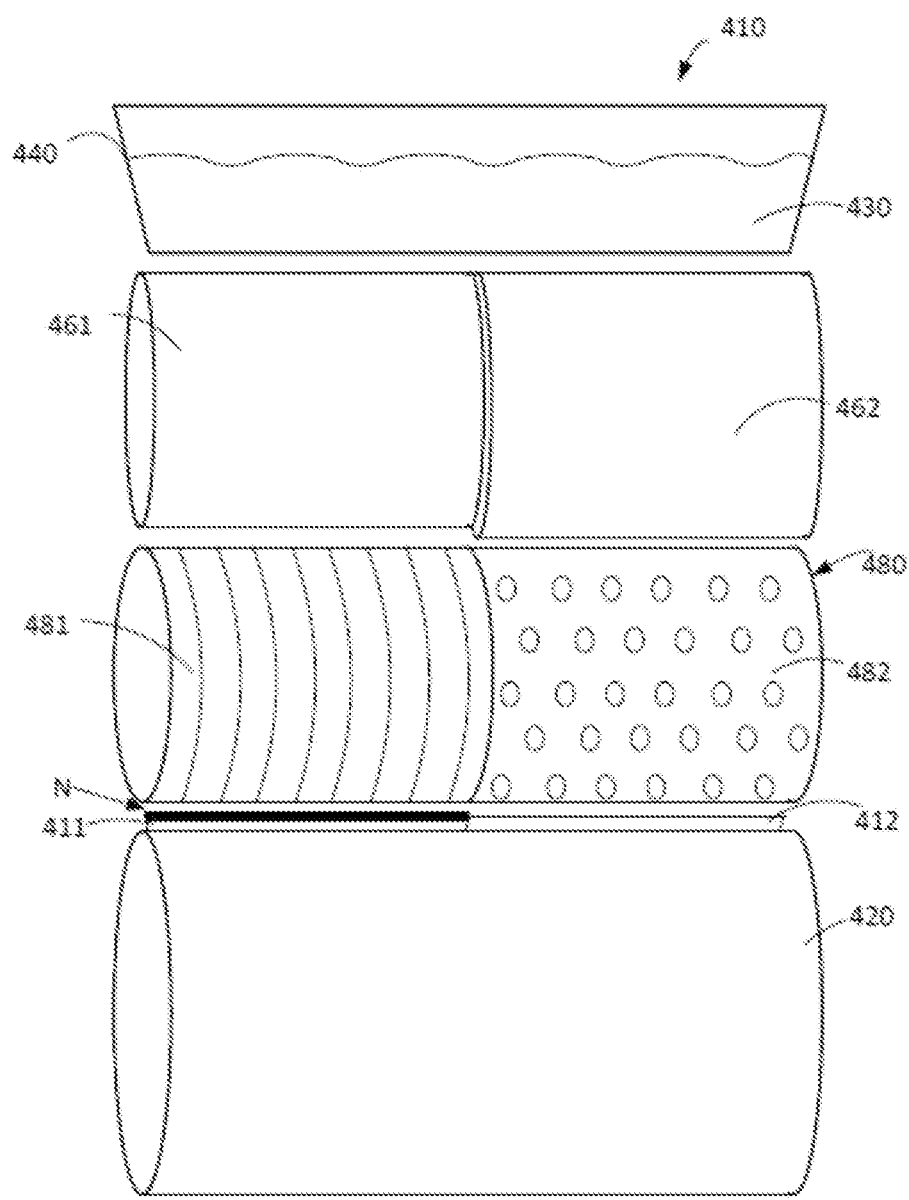
FIG. 5 is a schematic front view of a flexographic printing unit according to a further embodiment.
Figure 5A:
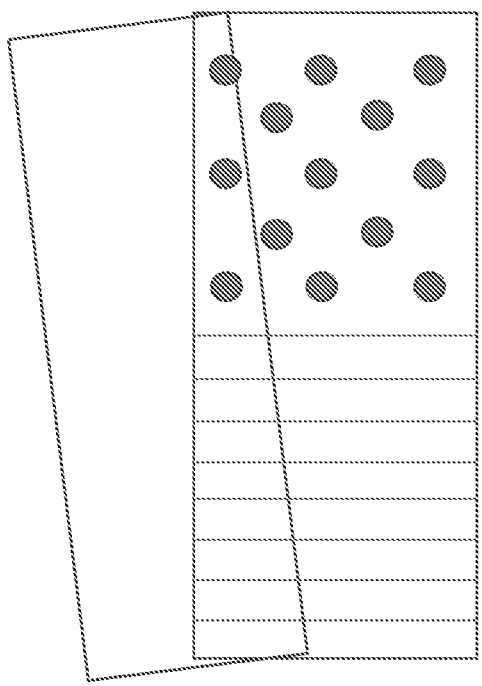
FIG. 5a is a schematic view of an anilox roller of a flexographic printing unit arranged at an incline relative to a center axis of a printing roller of a flexographic printing unit according to a further embodiment.

With reference to FIG. 5, a further example of a flexographic printing unit 410 in a flexographic printing device is shown which printing unit 410 is configured for simultaneously printing at least two material webs 411, 412 having different thicknesses. The embodiment shown could be an alternative to the above-mentioned embodiments or it could be used in combination with any one of the above-described embodiments. As in the examples above, the first material web 411 is thicker than the second material web 412. The printing unit 410 comprises a printing ink chamber 440 for a printing ink 430, and two anilox rollers 461, 462, which transfer the printing ink to the printing roller 480 comprising two printing clichés 481 and 482. It should be clear that only one large printing cliché with two separate printing patterns could be used instead. In the illustrated example, the radial extension of the anilox roller 461 and anilox roller 462, respectively is adapted in respect to the thickness of the material web 411 and 412 to be printed. In the illustrated example, the printing unit 410 comprises an equal amount of anilox rollers and material webs, and each of the anilox rollers 461 and 462 has a radial extension adapted to the thickness of the respective material web 411, 412 to be printed. In connection with anilox rollers and as shown in FIG. 5, the anilox rollers 461, 462 may have substantially the same radius, but the radial position of each of the anilox rollers is adapted to the thickness of the respective material web to be printed. Thereby, the radial extension in respect of the material webs to be printed is adapted. The first anilox roller 461 is located at a larger distance from the first cliché 481 mounted on the printing roller 480, since it is adapted to feed ink 440 to the first cliché which prints on the first material web 411, which is thicker than the second material web 412. In an alternative variant, which is not shown, the anilox roller could be a single anilox roller as in connection with the embodiments shown in FIGS. 3 and 4. To provide different amount of ink to the respective cliché 481, 482, the anilox roller could be inclined in an axial direction, meaning that the anilox roller is tilted in respect of the center axis of the printing roller 480, which normally has its center axis parallel to the center axis of the anilox roller 460. By inclined in axial direction is thus meant that a center axis of the anilox roller is inclined compared to a plane of the center axis of the printing roller.

All the variants for the printing unit described above in connection with FIG. 3-5 could be combined in any manner. For example, it could be possible to use all the variants or combine a thicker cliché shown in FIG. 3 with the impression cylinder of FIG. 4 and/or the anilox roller/rollers described in connection with FIG. 5. Also, the printing device may comprise more than one printing unit as described above. For example in the printing device there may be from 1 to 8 printing units as described above. The printing units may be configured to print different colors or coat the material web with a substance. If more than 8 units were needed, several printers could be positioned after each other, and in this way it would be feasible to have even more units in the printing process.

The present disclosure also relates to a method of simultaneously printing at least two material webs having different thicknesses in a printing device comprising a printing unit as described above. In the method the printing unit is adapted to print the webs by arranging:

I. the radial extension of the surface of the printing roller carrying the image to be printed such that it is adapted in respect to the thickness of the respective material web to be printed; and/or II. the surface of the impression roller such that the radial extension along the surface of the impression roller is adapted to the thickness of the material webs to be printed; and/or III. the surface of the anilox roller such that the radial extension along the surface of the anilox roller is adapted to the thickness of the material web to be printed by arranging a respective anilox roller to the respective material web and/or by axially inclining the anilox roller.

The steps I, II and II may be performed as described above in connection with FIG. 3-5.

As mentioned above the at least one printing cliché may comprise a first printing pattern zone adapted to print on the first material web and a second printing pattern zone adapted to print on the second material web. Alternatively, a first printing cliché comprising a first printing pattern is configured to print on the first material web and a second printing cliché comprising a second printing pattern is configured to print on the second material web.

Figure 6:
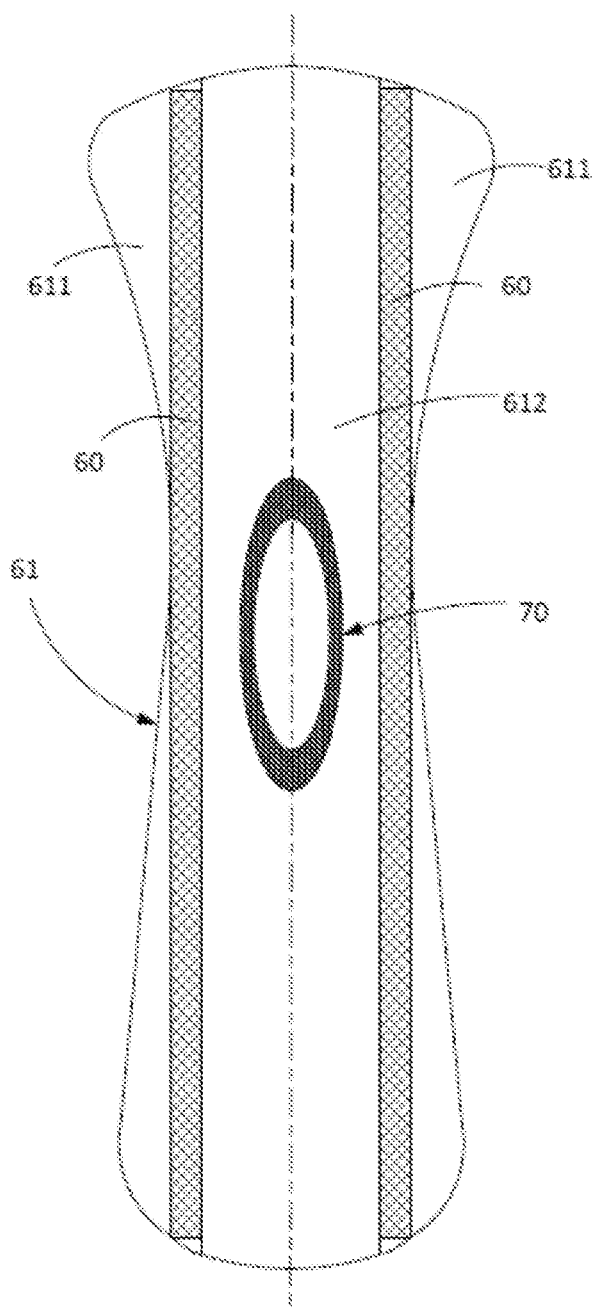
FIG. 6 is a schematic top view of an absorbent article with two printed nonwoven materials having different thicknesses, prepared according to the embodiments described herein.

It should be noted that more than two webs could be printed. For example three material webs can be printed. The method thus comprises printing on the three material webs having at least two different thicknesses, and wherein the printing roller comprises a printing cliché for the respective material web. All three material webs may have different thicknesses or two of the material webs may have the same thickness. For example, if the material web is to be used in a diaper, incontinence article or a sanitary napkin, the two outermost material webs may be thicker than the material web located between the outermost material webs. In this way it could be possible to provide a printed web suitable for use in an absorbent article as schematically shown in FIG. 6 and provide soft side edges for the article. The absorbent article comprises a topsheet comprising thicker side edge portions 611 with a first printed image 60. The middle section 612 of the article 61 comprises a thinner nonwoven material provided with a second printed image 70. The side edge portions 611 and the middle section of the topsheet are connected to each other, e.g., by gluing or welding the webs together. The first printed image 60 may be used to hide a connecting seam.

In the method the first material web and the second material web may be simultaneously fed to the printing unit where a respective printing pattern on the respective first and second webs is printed. In the method, the first material web and the second material web may be separate webs, and wherein the method comprises feeding the webs from separate feeding devices or master rolls. Alternatively, the first material web and the second material web may be connected to each other in a parallel manner, such as by welding or gluing, and the method may thus comprise feeding the webs from a common feeding device comprising a common master roll. Also, as is clear more than two material webs can be printed simultaneously. However, the amount of material webs to be printed simultaneously is up to and including six material webs. For example, in case of three material webs, the webs may be separate webs and the method may comprise feeding the webs from separate feeding devices. Alternatively, and as mentioned above, the three material webs may be connected to each other in a parallel manner, such as by welding or gluing, and the method comprises feeding the webs from a common feeding device.

According to a variant, and as also shown in connection with FIGS. 3 to 5 the printing patterns provided by the first and second clichés may be different from each other.

The present disclosure also relates to the material web printed by the method as described above. Since the printing unit is adapted to the different material thicknesses, it is possible to provide a printed material web with equal printing quality in all webs. The material web may be a nonwoven, a plastic film, a woven material, a laminate or a combination thereof.

Suitably, the printed material web is used in a hygiene absorbent article comprising a topsheet, backsheet, an absorbent core between the topsheet and the backsheet, and optionally side panels, leg elastics, waist elastics and/or a belt.

Although the above discussion has been exemplified through a sanitary napkin, the present invention is also applicable to other absorbent articles such as diapers, incontinence pads or panty-liners. For instance, application of the invention to diapers would provide similar benefits in terms of comfort, fit and leakage-prevention.

The embodiments described above are only descriptions of preferred embodiments of the present invention, and do not intended to limit the scope of the present invention. Various variations and modifications can be made to the technical solution of the present invention by those of ordinary skills in the art, without departing from the design and spirit of the present invention. The variations and modifications should all fall within the claimed scope defined by the claims of the present invention.

What is claimed is:

1. A flexographic printing device comprising a printing unit comprising:
a printing roller carrying on a surface thereof an image to be printed, an impression roller having a surface, and an anilox roller adapted to feed printing ink from a printing ink chamber onto the printing roller,
wherein the printing unit is configured for simultaneously printing at least two material webs having different thicknesses, the at least two material webs being printed when they pass a printing nip formed between the printing roller and the impression roller, and
wherein a radial extension of the anilox roller is adapted in respect to the thickness of the material web to be printed and the anilox roller is axially inclined to adapt the radial extension of the anilox roller to the thickness of the respective material web to be printed.

2. The flexographic printing device of claim 1, wherein the image to be printed is provided as a cliché mounted on the printing roller.

3. The flexographic printing device of claim 2, wherein an amount of clichés is equal to an amount of material webs to be printed and wherein at least one of the clichés has a radial extension adapted to the thickness of the respective material web to be printed.

4. The flexographic printing device of claim 3, wherein the surface of the impression roller has an equal amount of surface zones as there are material webs, and wherein a radial extension of the impression roller at each of the surface zones is adapted to the thickness of the respective material web to be printed,
wherein the printing unit comprises an equal amount of anilox rollers as there are material webs, and wherein the radial extension of each of the anilox rollers or the radial position of each of the anilox rollers is adapted to a thickness of the respective material web to be printed,
wherein the surface zones of the impression roller each comprise a cover having a radial extension adapted to the thickness of the respective material web to be printed, and
the flexographic printing device further comprises:
at least one feeding device for the at least two material webs.

5. The flexographic printing device of claim 1, wherein the image to be printed is provided as an engraved printing sleeve or as an engraved printing roller.

6. The flexographic printing device of claim 1, wherein the surface of the impression roller has an equal amount of surface zones as there are material webs, and wherein at least one of the surface zones has a radial extension adapted to the thickness of the respective material web to be printed.

7. The flexographic printing device of claim 6, wherein the surface zones of the impression roller each comprise a cover having the radial extension adapted to the thickness of the respective material web to be printed.

8. The flexographic printing device of claim 1, wherein the printing unit comprises an equal amount of anilox rollers as there are material webs, and wherein the radial extension of each anilox roller of the plurality of anilox rollers is adapted to a thickness of the respective material web to be printed.

9. The flexographic printing device of claim 1, further comprising:
at least one feeding device for the at least two material webs.

10. A method of simultaneously printing at least two material webs having different thicknesses in a printing device, comprising:
feeding printing ink from a printing ink chamber onto a printing roller using an anilox roller;
moving at least two material webs having different thicknesses through a printing nip defined between the printing roller and an impression roller, the printing roller carrying on a surface thereof an image to be printed and the impression roller having a surface, to thereby print the image onto the at least two material webs; and
adapting the printing device by arranging at least one of the following (I)-(III):
I. a radial extension of the surface of the printing roller carrying the image to be printed such that it is adapted in respect to a thickness of the respective material web to be printed;
II. the surface of the impression roller such that a radial extension along the surface of the impression roller is adapted to the thickness of the material webs to be printed; and
III. a surface of the anilox roller such that a radial extension along the surface of the anilox roller is adapted to the thickness of the material web to be printed.

11. The method of claim 10, wherein the image to be printed is provided in the form of one of the following: at least one printing cliché, an engraved printing sleeve, and as an engraved printing roller comprising an equal amount of printing pattern zones as an amount of the material webs to be printed.

12. The method of claim 11, wherein the image to be printed is provided as printing clichés, with an amount of printing clichés corresponding to the amount of the material webs, and wherein each of the printing clichés is configured to print on the respective material web.

13. The method of claim 12, wherein the printing patterns provided by the printing clichés are different from each other.

14. The method of claim 10, wherein the method further comprises simultaneously feeding the material webs to the printing unit and printing a respective printing pattern on the respective webs.

15. The method of claim 10, wherein the material webs are separate webs, and wherein the method comprises feeding the material webs from separate feeding devices.

16. The method of claim 10, wherein the material webs are connected to each other in a parallel manner, and the method comprises feeding the material webs from a common feeding device.

17. The method of claim 10, wherein the amount of material webs is two.

18. The method of claim 10, wherein the amount of material webs is three, and wherein two of the three material webs have a same thickness and one of the material webs is thicker or thinner than the two having the same thickness.

19. The method of claim 10, further comprising:
printing a material defining the at least two material webs that includes one or more of: a nonwoven, a plastic film, a woven material, and a laminate, and
incorporating the at least two material webs in a hygiene absorbent article comprising a topsheet, backsheet, and an absorbent core between the topsheet and the backsheet.

* * * * *